United States Patent
Morimoto

(10) Patent No.: US 10,398,607 B2
(45) Date of Patent: Sep. 3, 2019

(54) ABSORBENT ARTICLE HAVING ELASTIC BELT

(71) Applicant: The Procter & Gamble Company, Cincinnati, OH (US)

(72) Inventor: Koichi Morimoto, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 470 days.

(21) Appl. No.: 14/971,069

(22) Filed: Dec. 16, 2015

(65) Prior Publication Data
US 2016/0184145 A1    Jun. 30, 2016

(30) Foreign Application Priority Data

Dec. 25, 2014 (WO) ................ PCT/CN2014/094895

(51) Int. Cl.
*A61F 13/15* (2006.01)
*A61F 13/49* (2006.01)
*A61F 13/496* (2006.01)

(52) U.S. Cl.
CPC ...... *A61F 13/49011* (2013.01); *A61F 13/496* (2013.01); *A61F 13/4902* (2013.01); *A61F 13/49012* (2013.01); *A61F 13/49014* (2013.01); *A61F 2013/49026* (2013.01); *A61F 2013/49028* (2013.01); *A61F 2013/49033* (2013.01); *A61F 2013/49036* (2013.01)

(58) Field of Classification Search
CPC .......... A61F 13/49014; A61F 13/49011; A61F 13/49012; A61F 13/4902; A61F 2013/49026; A61F 2013/49028

USPC ....... 604/385.3, 385.24, 385.25, 385.26, 396
See application file for complete search history.

(56) References Cited

U.S. PATENT DOCUMENTS

| 4,919,738 A | 4/1990 | Ball et al. |
| 5,340,648 A | 8/1994 | Rollins et al. |

(Continued)

FOREIGN PATENT DOCUMENTS

| EP | 2659870 A1 | 11/2013 |
| JP | 2008253583 | 10/2008 |

(Continued)

OTHER PUBLICATIONS

PCT International Search Report, dated Feb. 23, 2017 (10 pages).
PCT International Search Report, dated Aug. 24, 2015 (7 pages).
PCT Written Opinion dated Jun. 27, 2017.

*Primary Examiner* — Jacqueline F Stephens
(74) *Attorney, Agent, or Firm* — Daniel S. Albrecht; Christian M. Best; William E. Gallagher

(57) ABSTRACT

An absorbent article including a main body with an absorbent core, and a ring-like elastic belt, is disclosed. The article may include a front belt and a back belt each formed by an inner sheet, an outer sheet and a plurality of elastic bodies sandwiched therebetween and running in the transverse direction. The elastic bodies in the back belt may include a plurality of waist elastic bodies having elasticity over the entire transverse width of the back belt; a plurality of tummy elastic bodies removed of their elasticity in at least a portion overlapping the absorbent core, and a core edge elastic body disposed overlapping the absorbent core and adjacent the distal edge of the absorbent core, the core edge elastic body having elasticity over the entire transverse width of the back belt.

12 Claims, 5 Drawing Sheets

(56) References Cited

U.S. PATENT DOCUMENTS

| | | |
|---|---|---|
| 5,382,400 A | 1/1995 | Pike et al. |
| 5,415,649 A | 5/1995 | Watanabe et al. |
| 5,418,045 A | 5/1995 | Pike et al. |
| 5,501,756 A | 3/1996 | Rollins et al. |
| 5,507,909 A | 4/1996 | Rollins et al. |
| 5,622,722 A | 4/1997 | Stokes et al. |
| 5,707,468 A | 1/1998 | Arnold et al. |
| 6,077,375 A | 6/2000 | Kwok |
| 6,200,635 B1 | 3/2001 | Kwok |
| 6,235,137 B1 | 5/2001 | Van Eperen et al. |
| 6,361,634 B1 | 3/2002 | White et al. |
| 6,375,646 B1 | 4/2002 | Widlund et al. |
| 6,454,989 B1 | 9/2002 | Neely et al. |
| 6,520,237 B1 | 2/2003 | Bolyard et al. |
| 6,561,430 B2 | 5/2003 | Ou |
| 6,582,518 B2 | 6/2003 | Riney |
| 6,610,161 B2 | 8/2003 | Erdman |
| 6,613,146 B2 | 9/2003 | Bolyard |
| 6,632,385 B2 | 10/2003 | Kauschke et al. |
| 6,632,386 B2 | 10/2003 | Shelley et al. |
| 6,645,569 B2 | 11/2003 | Cramer et al. |
| 6,652,693 B2 | 11/2003 | Burriss et al. |
| 6,719,846 B2 | 4/2004 | Nakamura et al. |
| 6,737,102 B1 | 5/2004 | Saidman et al. |
| 6,803,103 B2 | 10/2004 | Kauschke et al. |
| 6,863,933 B2 | 3/2005 | Cramer et al. |
| 7,112,621 B2 | 9/2006 | Rohrbaugh et al. |
| 7,291,239 B2 | 11/2007 | Polanco et al. |
| 7,331,946 B2 | 2/2008 | Shimada et al. |
| 7,858,544 B2 | 12/2010 | Turi et al. |
| 8,186,296 B2 | 5/2012 | Brown et al. |
| 8,308,706 B2 | 11/2012 | Rukae |
| 8,445,744 B2 | 5/2013 | Autran et al. |
| 8,475,424 B2 | 7/2013 | Fujimoto et al. |
| 8,500,710 B2 | 8/2013 | Takino et al. |
| 8,518,009 B2 | 8/2013 | Saito et al. |
| 8,728,051 B2 | 5/2014 | Lu et al. |
| 2005/0008839 A1 | 1/2005 | Cramer et al. |
| 2005/0107763 A1 | 5/2005 | Matsuda et al. |
| 2006/0025746 A1 | 2/2006 | Sasaki et al. |
| 2006/0030831 A1 | 2/2006 | Matsuda et al. |
| 2011/0071488 A1* | 3/2011 | Kuwano ........... A61F 13/49001 604/385.3 |
| 2013/0211363 A1 | 8/2013 | LaVon et al. |
| 2013/0310785 A1 | 11/2013 | Wade et al. |
| 2013/0324957 A1 | 12/2013 | Gassner et al. |
| 2015/0019958 A1 | 1/2015 | Yoshioka |

FOREIGN PATENT DOCUMENTS

| | | |
|---|---|---|
| JP | 2009125088 | 6/2009 |
| JP | 2011-115304 A | 6/2011 |
| JP | 2013123447 A | 6/2013 |
| WO | WO 2014-122980 A1 | 8/2014 |
| WO | WO 2014-192981 A1 | 12/2014 |
| WO | WO 2014-203679 A1 | 12/2014 |

* cited by examiner

ABSORBENT ARTICLE HAVING ELASTIC BELT

FIELD OF THE INVENTION

The present invention relates to absorbent articles having an elastic belt having elastic bodies overlapping the absorbent core.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often children who are toilet training, as well as for younger children who become more active in movement such that application of taped-type absorbent articles tends to be more difficult.

Many pant-type absorbent articles use elastic elements secured in an elastically contractible condition in the waist and/or leg openings. Typically, in order to insure full elastic fit about the leg and the waist such as is provided with durable undergarments, the leg openings and waist opening are encircled at least in part with elasticized elements positioned along the periphery of the respective opening.

Pant-type absorbent articles having a main body to cover the crotch region of the wearer and a separate elastic belt defining the waist opening and leg opening are known in the art, such as described in PCT Publication WO 2006/17718A. Such pant-type absorbent articles may be referred to as belt-type pants. Belt-type pants are advantageous in that they have good breathability around the elastic belt, and in that they may be manufactured economically. Belt-type pants may be removed of elasticity of the elastic belt where the elastic belt overlaps the absorbent core, for avoiding bunching up of the absorbent core. Such removal of elasticity may provide a gap between the area where the absorbent core overlaps and not. Such gap may interfere with bringing the absorbent core close to the wearer. Further, in that the gap obviates the existence of an absorbent core, this may negatively affect a garment like appearance.

Based on the foregoing, there is a need for a pant-type absorbent article having balanced performance such as fit, comfort during wear, prevention of sagging, and prevention of leakage, while also providing a garment like appearance. There is further a need for providing such an absorbent article in an economical manner.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1:
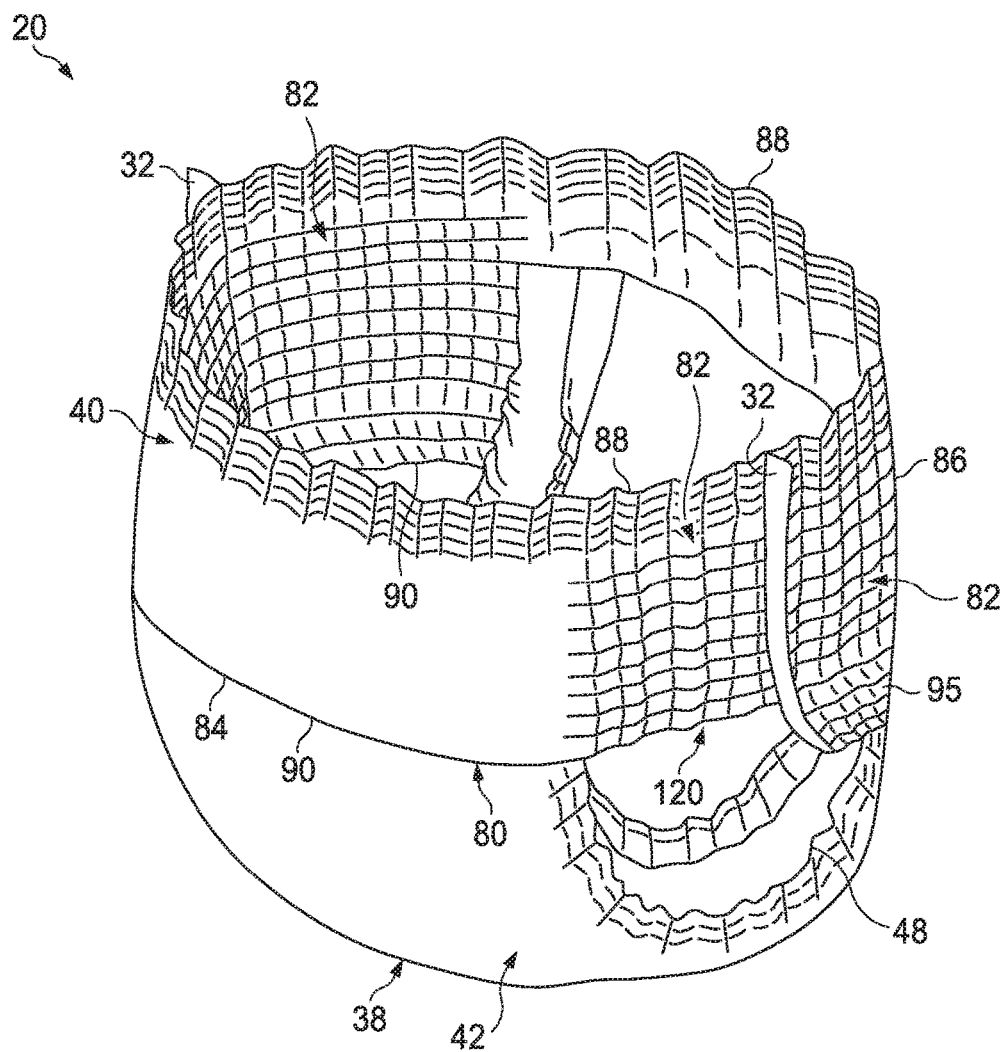
FIG. 1 is a perspective view of one embodiment of an absorbent article of the present invention.

As used herein, the following terms shall have the meaning specified thereafter:

"Absorbent article" refers to articles of wear which may be in the form of pants, taped diapers, incontinent briefs, feminine hygiene garments, and the like configured to also absorb and contain various exudates such as urine, feces, and menses discharged from the body. The "absorbent article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF EXAMPLES

Figure 2:
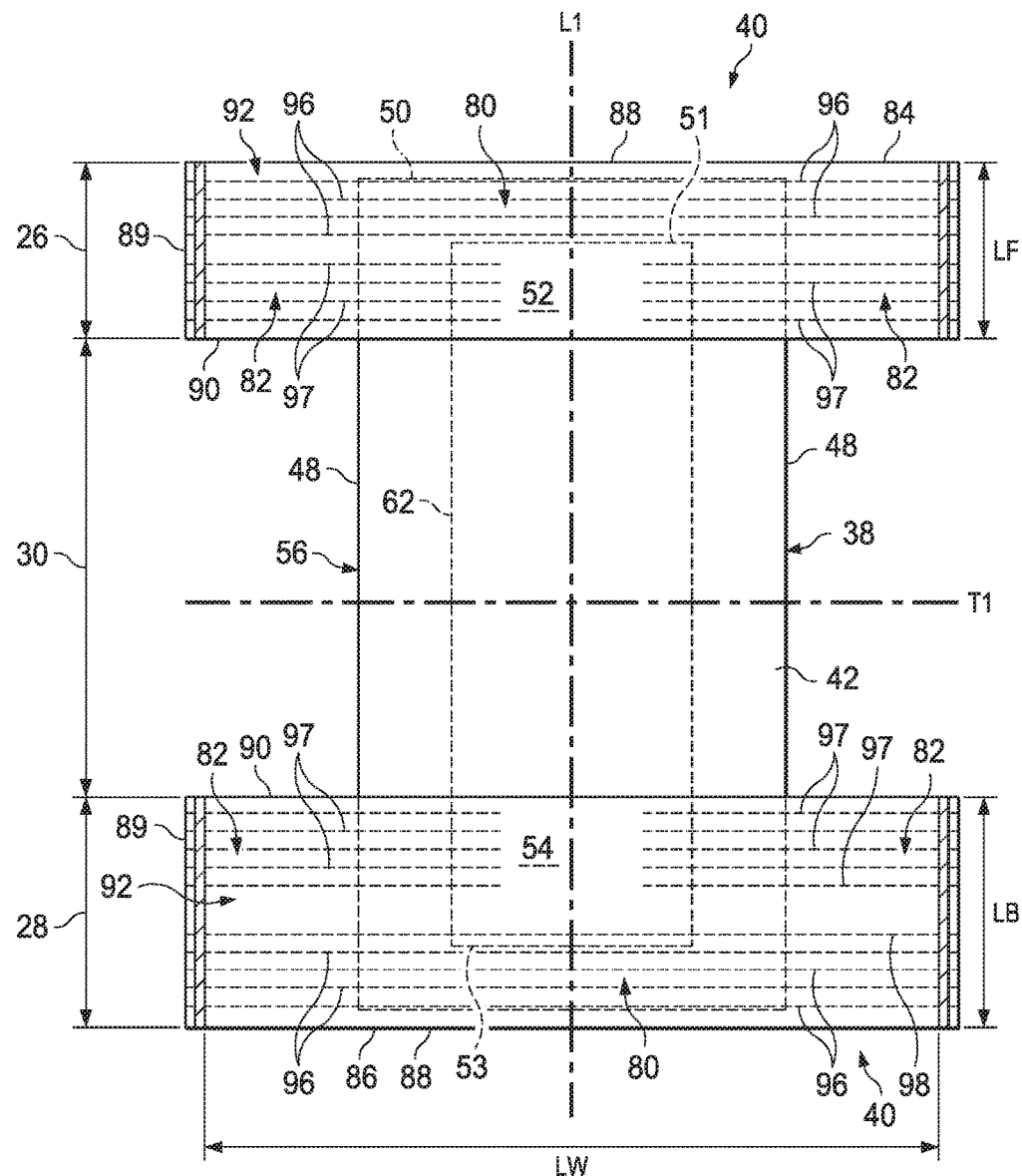
FIGS. 2-4 are schematic plan views of embodiments of an absorbent article of the present invention in a flat uncontracted condition showing the garment facing surface.

FIG. 1 is a perspective view of an embodiment of the absorbent article 20 of the present invention and FIG. 2 is a schematic plan view of the same article with the seams unjoined and in its flat uncontracted condition showing the garment-facing surface. The absorbent article 20 has a longitudinal centerline L1 which also serves as the longitudinal axis, and a transverse centerline T1 which also serves as the transverse axis. The absorbent article 20 has a skin-facing surface, a garment-facing surface, a front region 26, a back region 28, a crotch region 30, and seams 32 which join the front region 26 and the back region 28 to form two leg openings and a waist opening. The absorbent article 20 comprises a main body 38 to cover the crotch region of the wearer, a front belt 84 and a back belt 86 (hereinafter may be referred to as "front and back belt"), the front and back belts 84, 86 forming a ring-like elastic belt 40 (hereinafter may be referred to as "waist belt") extending transversely defining the waist opening. The front and back belts 84, 86 and the main body 38 jointly define the leg openings.

The main body 38 may contain an absorbent core 62 for absorbing and containing body exudates disposed on the main body 38. In the embodiment shown in FIG. 2, the main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the absorbent article 20, a back waist panel 54 positioned in the back region 28, and a crotch panel 56 between the front and back waist panels 52, 54 in the crotch region 30. The center of the front belt 84 is joined to a front waist panel 52 of the main body 38, the center of the back belt 86 is joined to a back waist panel 54 of the main body 38, the front and back belt 84, 86 each having a left side panel and a right side panel 82 where the main body 38 does not overlap. The absorbent core 62 may take a rectangular shape, hour glass shape, or I-shape. The absorbent core 62 may have regions devoid of absorbent material for conforming to the wearer's body before or after wetting. The absorbent core 62 comprises substantially linear distal edges in the longitudinal direction disposed on the front belt 84 and the back belt 86.

Referring to FIGS. 1 and 2, the ring-like elastic belt 40 formed by the front belt 84 and back belt 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel 56 of the main body 38 than the position of a "distal" portion. Therefore, the proximal edge 90 is located closer than the waist edge or distal edge 88 relative to the crotch panel 56 of the main body 38. The front and back belts 84, 86 may be joined with each other only at the side edges 89 at the seams 32 to form a absorbent article having a waist opening and two leg openings. Each leg opening may be provided with elasticity around the perimeter of the leg opening by the combination of elasticity from the front belt 84, the back belt 86, and any from the main body 38. The front leg opening region 120 is disposed adjacent the leg opening along the leg edge or proximal edge 90 of the left and right side panels 82 of the front belt 84.

The front and back belts 84, 86 are discontinuous with one another in the crotch region 30. In such embodiment, there is no material that covers the entirety of either the wearer-facing surface or garment-facing surface of the article. The front central panel 80 may partly overlap with the front waist panel 52 of the main body 38. The back central panel 80 may partly overlap with the back waist panel 54 of the main body 38. However, the central panels 80 may not extend into the crotch panel 56 of the main body 38 and not be disposed in the crotch panel 56. In the embodiment shown in FIG. 2, the central panels 80 partly overlap with and are joined to the front waist panel 52 and the back waist panel 54, respectively.

Referring to FIG. 2, the front belt 84 and back belt 86 may each comprise an inner sheet 94, an outer sheet 92, (hereinafter also collectively "belt sheets") and a plurality of elastic bodies sandwiched therebetween and running in the transverse direction substantially parallel to each other, and configured to impart elasticity per each zone according to the relationship described below. (The inner sheet 94 is not shown.) Such an article may be economically made.

In one embodiment, the transverse width LW of the back belt 86 in the uncontracted condition may be the same as the transverse width of the front belt 84 of the same condition. In one embodiment, each of the proximal edges 90 and the distal edges 88 of the front belt 84 and the back belt 86 may be substantially parallel, as in FIG. 2.

In one embodiment, the longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such embodiment, the seams 32 close the front and back belt 84, 86 side edges 89 of the same length for forming the article. Such an article may be economically made.

Figure 3:
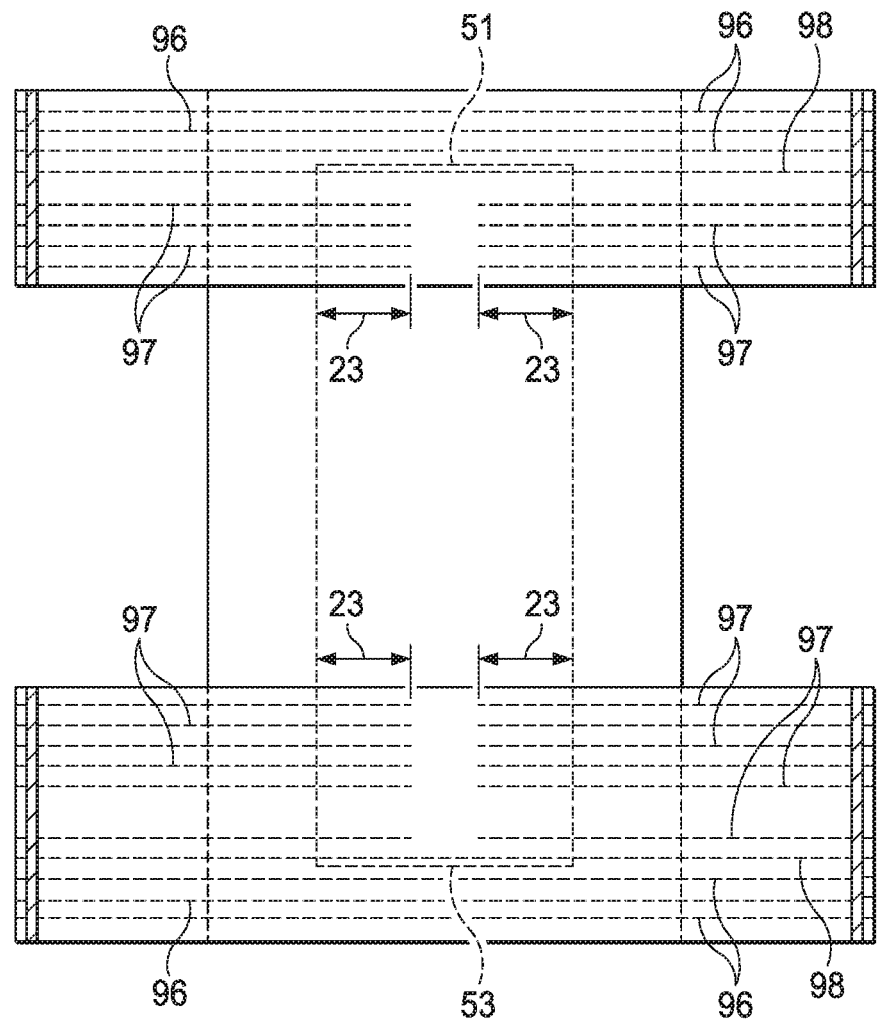

In one embodiment, the back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1-3). In such embodiment, when the absorbent article is assembled to form the waist opening and the leg openings, the absorbent article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Whether or not the longitudinal length LB of the back belt 86 and the longitudinal length LF of the front belt 84 are the same, the entirety of the longitudinal length LF of the belt side edge 89 of the front belt 84 is seamed with the belt side edge 89 of the back belt 86 to define a seam length LS, as in FIG. 3. When the front belt 84 has straight distal edges 88 and proximal edges 90 that are substantially parallel with each other, then the longitudinal length LF of the front belt 84 is equal to the seam length LS.

In one embodiment, the outer sheet 92 of the front or back belt 84, 86 towards the distal edge 88 may be longer than the size of the inner sheet 94 in the longitudinal direction, and an end flap of the outer sheet 92 may be folded over the distal end of the inner sheet 94 at the waist opening. The front and back belts 84, 86 may be provided in non-woven material having a basis weight of less than 45 gsm for sake of breathability perception and softness of the belt 40.

The tensile stress (N/m) of the front and back elastic belts 84, 86, respectively, may be profiled in order to provide the benefits of the present invention. The waist belt 40 exhibits elasticity due to the plurality of elastic bodies running in the transverse direction, wherein the elastic bodies adhered to the inner and outer sheets 92, 94 impart elasticity to the waist belt 40. Tensile stress of the waist belt 40 may be adjusted by one or more of the following methods; 1) elongation rate of the elastic bodies; 2) density (dtex) of the elastic bodies; 3) longitudinal interval of multiple elastic bodies; and 4) effective length of elasticity of the elastic bodies in the transverse direction. By elongation, "0% elongation" means the original unstrained length of the elastic body. Each elastic body disposed on the waist belt 40 may be disposed over the entire transverse width LW. Some elastic bodies may be removed of its elasticity contributing to the elasticity of the waist belt 40 in the transverse center of the front and/or back belt 84, 86. When a portion of an elastic body is not contributing to the elasticity of the waist belt 40, the remainder of the intact elastic body capable of imparting elasticity to the waist belt 40 is defined as the "effective length of elasticity of an elastic body". An elastic body unadhered to the inner and outer sheets 92, 94 may be left dangling, thereby still exhibiting elasticity as an elastic body per se. However, so long as the elasticity is non-contributory to elasticity of the waist belt 40, such length or area is described herein as "non-elastic". The elastic bodies disposed on the front and/or back belt 84, 86 may be treated such that certain of the area overlapping the front and/or back waist panels 52, 54 of the main body 38 are removed of elasticity. Removal of elasticity from at least a portion of the area overlapping the absorbent core 62 in the back belt, or both the front and back belt, may be advantageous, in that elasticity in the front and/or back area may cause bunching of the absorbent core 62 and interfere with close fit of the main body 38 to the wearer.

In the present invention, the elastic bodies disposed on at least the back belt 86, and optionally the front belt 84, comprises:

a plurality of waist elastic bodies 96 disposed between the distal edge 51, 53, of the absorbent core 62 and the distal edge 88 of the belt, the waist elastic bodies 96 having elasticity over the entire transverse width LW of the back belt 86 and optionally the front belt 84;

a plurality of a tummy elastic bodies 97 disposed overlapping the absorbent core 62 and removed of its elasticity in at least a portion overlapping the absorbent core 62, wherein all elastic bodies but a single core edge elastic body 98 overlapping the absorbent core 62 are removed of its elasticity in at least a portion; and the core edge elastic body 98 disposed overlapping the absorbent core 62 and adjacent the distal edge 51, 53 of the absorbent core, the core edge elastic body 98 having elasticity over the entire transverse width LW of the back belt 86 and optionally the front belt 84.

The waist elastic bodies 96 herein are disposed between the distal edge 51, 53, of the absorbent core 62 and the distal edge 88 of the waist belt, the waist elastic bodies 96 having elasticity over the entire transverse width LW of the back belt 86 and optionally the front belt 84. When the waist elastic bodies 96 are disposed on both the front and back belts 84, 86, at least some of the waist elastic bodies 96 may be matched at the seams 32 to provide good fit and prevent sagging of the entire article, as well as provide a waist band appearance around the waist opening.

The tummy elastic bodies 97 herein are disposed in the longitudinal direction overlapping the absorbent core, and removed of its elasticity in at least a portion overlapping the absorbent core 62. Such removal of elasticity in a certain portion may be referred to herein as tummy cut. The tummy elastic bodies 97 are tummy cut at approximately the center of the waist belt along the longitudinal axis, while leaving an effective length of elasticity of an elastic body to create side panels 82. By tummy cut, at least a certain area of the back belt 86, and optionally the front belt 84, overlapping the absorbent core 62 is rendered non-elastic.

Figure 4:
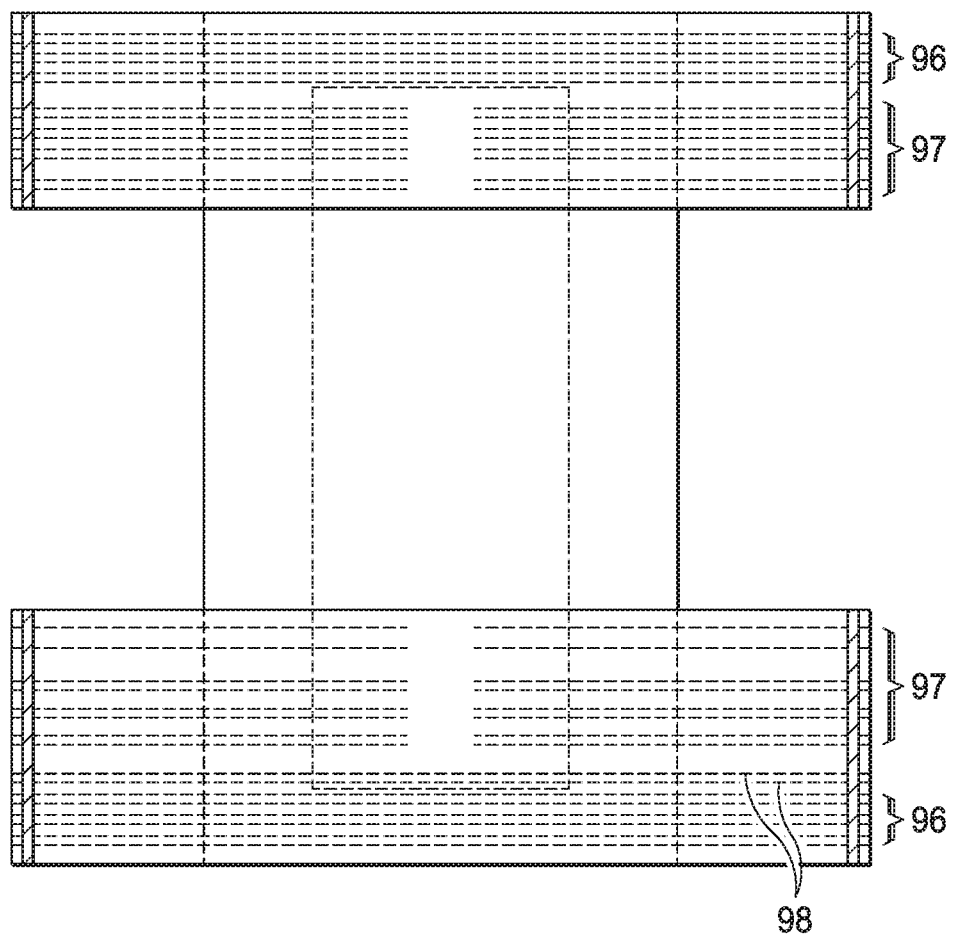

The core edge elastic body 98 herein is may be a single elastic body as in FIGS. 2 and 3, or an array of 2 elastic bodies disposed in the interval in the longitudinal direction of no more than 4 mm as in FIG. 4. Without intending to be bound by theory, it is believed that by disposing the elastic body(ies) 98 in a close proximity of no more than 4 mm to each other, the array exhibits a behavior as if it were one elastic body with a certain width, and provides various benefits. For example, the array provides more or less the combined tensile force of the elastic bodies 98 in the array, such that each elastic body may be disposed at a much lower tensile force. The elastic body for forming the core edge elastic body 98 may have a density of 470-1100 dtex, and disposed at an elongation of from 150% to 300%.

Without intending to be bound by theory, it is believed that the core edge elastic body 98 prevents creating a gap between the area where the absorbent core overlaps and not, by providing a gradation of tensile stress between the area where the waist elastic bodies 96 are disposed, and the area where the tummy elastic bodies 97 do not exhibit elasticity. By having just one or one array of a core edge elastic body 98, the absorbent core 62 may be fit closer to the wearer, while also avoiding bunching up of the majority of the area of the absorbent core 62 overlapping with the waist belt 40. Further, by preventing creation of such a gap which may obviate the existence of the absorbent core 62, the absorbent article may have a garment like appearance.

For effectively preventing the gap, the core edge elastic body 98 may be disposed at a distance of from 1 mm to 30 mm, or from 3 mm to 20 mm away from the distal edge 51, 53 of the absorbent core 62. The relationship between the core edge elastic body 98 and the waist elastic bodies 96 disposed adjacent the core edge elastic body 98 may be adjusted to further effectively prevent the gap. The waist elastic bodies disposed adjacent the core edge elastic body may be disposed at a distance of from 2 mm to 20 mm, or from 3 mm to 20 mm of the distal edge 51, 53 of the absorbent core 62. The waist elastic bodies disposed adjacent the core edge elastic body may have a density of 470-1100 dtex, and disposed at an elongation of from 150-250%.

In one embodiment, the main body 38 may be joined to the front and back belts 84, 86, such that the transverse centerline of the absorbent core 62 does not match the transverse centerline T1 of the article. Such a configuration may be advantageous to provide the front or back region 26, 28 to have higher containment capacity compared to the other region. Accordingly, in this embodiment, when the front belt comprises the waist elastic bodies 96, tummy elastic bodies 97 and core edge elastic body 98, the core edge elastic body 98 of the front belt and back belt are disposed at different distances from the distal edge 88 of the waist belt in the longitudinal direction.

Referring to FIGS. 2-4, in one embodiment, the tummy elastic bodies 97 remain to have elasticity in regions overlapping the absorbent core adjacent the left and right transverse edges 23. Such transverse overlap region 23 further prevents creating a gap between the area where the absorbent core 62 overlaps and not along the transverse side edges of the absorbent core. Further, such configuration is advantageous for forming absorbent articles of small size. Namely, by providing a transverse overlap region 23 and instead decreasing the non-elastic region, the waist belt may be provided with a higher contraction level over the width of the waist belt 40, resulting in a smaller waist belt in the transverse direction in the contracted condition. Such small size article may have favorable fit. Further, in that the waist belt size in the contracted condition may be controlled to a greater degree, small size articles may be made even with waist belts having a relatively large transverse width LW in the uncontracted condition. This enables making articles of different sizes with the same transverse width LW in the uncontrated condition, which may be significantly cost effective. 11.

The article of the present invention may have a dimension of from 300 mm to 440 mm, or from 350 mm to 440 mm, in the longitudinal axis by using a total of no more than 40, or from 15 to 40 elastic bodies 96, 97, 98 for the elastic belt 40 per article. In the embodiments of FIGS. 3 and 4, the longitudinal ends of the main body 38 matches with the distal edges of the front and back belts 84, 86.

The article of the present invention may have a Waist Circumference Force provided by the elastic bodies 96, 97, 98 disposed on the waist belt 40 of no more than 10N, or no more than 8N, according to the Whole Article Force Measurement as described herein below. The Whole Article Force Measurement is for quantifying the force provided by the article 20 when stretched along the waist circumference, simulating initial stretch experience of the article 20 in the transverse direction when the user inserts hands in the article and expands the article. Namely, more or less the total tensile force provided by the elastic bodies 96, 97, 98 disposed in the transverse direction are measured. While there may be other elastic bodies disposed on the article, for example along the longitudinal side edges of the main body, the impact of such other elastic bodies are known to be small, when the user stretches the article in the transverse direction. The Whole Article Force Measurement is obtained by extending, or loading, the article in the transverse direction until a force of 19.6N is attained, wherein the force at the point where the belt 40 article reaches 70% of the maximum stretch is obtained. The force expected to be perceived by the user for expanding the article may be controlled, such that the user may experience a satisfying expansion of the belt 40 without excess effort.

The obtained wearable article of the present invention may provide fit, ease of application, prevention of leakage and gather marking around the leg opening. The obtained wearable article of the present invention may be made in an economical manner.

Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 5:
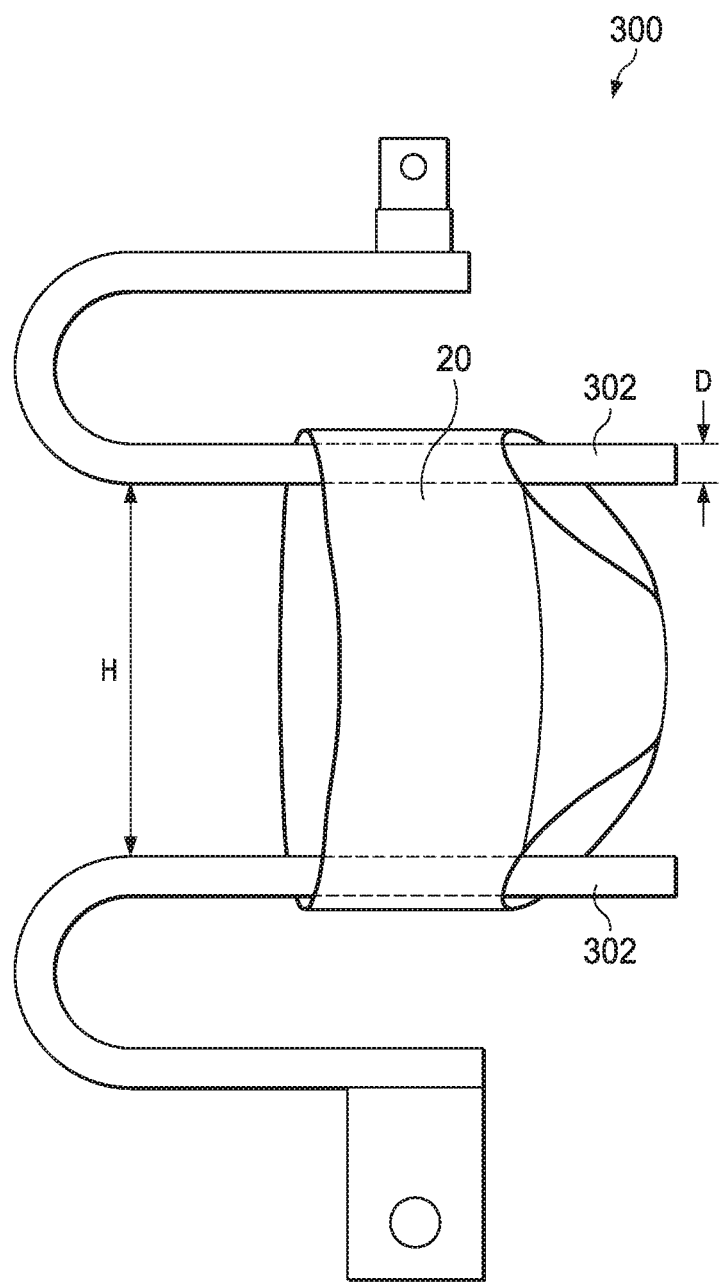
FIG. 5 is a schematic view of an example of a hanger-type sample holding fixture according to the "Whole Article Force Measurement".

The tensile tester is fitted with hanger-type sample holding fixtures 300 as shown in FIG. 5. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

$$\text{Gauge Circumference} = 2 \times (H + D + \pi D/2)$$

where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.61N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the initial gauge circumference at the same speed. The maximum circumference at 19.6N and the force at 70% stretch circumference during the extension segment of the test are recorded.

$$\text{Circumference (mm)} = 2 \times (H + D + \pi D/2)$$

The maximum circumference at 19.6N is defined as the Full Stretch Circumference (mm). The 70% stretch circumference is defined as the full stretch circumference×0.7. The Waist Circumference Force is defined as the force at 70% stretch circumference during the load (extension) segment of the test.

Five samples are analyzed and their average Initial Gauge Circumference, average Full Stretch Circumference and average Waist Circumference Force are calculated and reported to the nearest 1 mm, 1 mm and 0.01 N, respectively.

EXAMPLES

Examples 1 and 2

An absorbent article of the present invention having an elastic profiling according to FIGS. 2, 3, and Table 1 below having a belt width LW of 355 mm a front belt length LF of 85 mm, and a back belt length LB of 111 mm.

| Example | 1 (FIG. 3) | 2 (FIG. 2) |
|---|---|---|
| Size | NB(1) | S(2) |
| Front belt elastics distal side (dtex/prestretch %/#of elastics) | 940 dtex/275%/4 | 940 dtex/232%/4 |
| Front belt elastics proximal side with elastic cut window (dtex/prestretch %/#of elastics) | 680 dtex/275%/4 | 680 dtex/275%/4 |
| Back belt elastics distal side (dtex/prestretch %/#of elastics) | 940 dtex/275%/2<br>1100 dtex/275%/2 | 940 dtex/232%/2<br>1100 dtex/230%/2 |
| Back belt elastics proximal side with elastic cut window (dtex/prestretch %/#of elastics) | 680 dtex/275%/3 | 680 dtex/275%/3 |
| Back belt elastics buttock cover with elastic cut window (dtex/prestretch %/#of elastics) | 680 dtex/232%/1<br>1100 dtex/232%/1 | 680 dtex/232%/1<br>1100 dtex/232%/1 |
| Elastic cut window | 30 mm | 70 mm |
| Design weight range | 2~5 kg | 4~8 kg |
| Initial Gauge Circumference (IGC) | 209 mm | 238 mm |
| Distance between core edge elastic body and distal edge of absorbent core | Front: 3 mm<br>Back: 3 mm | 6.5 mm |
| Distance between adjacent waist elastic bodies and distal edge of absorbent core | Front: 6 mm<br>Back: 6 mm | 2.5 mm |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article continuous in a longitudinal direction and a transverse direction, comprising a main body and a ring-like elastic belt comprising a front belt and a back belt, a center of the front belt is joined to a front waist panel of the main body, a center of the back belt is joined to a back waist panel of the main body, the front and back belt each having a left side panel and a right side panel where the main body does not overlap, and transverse edges of the front belt and the back belt are joined by a seam to form a waist opening and two leg openings, wherein each of the front belt and back belt is formed by an inner sheet, an outer sheet, and a plurality of elastic bodies sandwiched therebetween and running in the transverse direction, and has a waist edge and a leg edge;

wherein the main body comprises an absorbent core, the absorbent core overlapping at least a portion of the front belt and the back belt;

wherein the elastic bodies disposed in one or both the front belt and the back belt comprise:

a plurality of waist band elastic bodies disposed between the distal edge of the absorbent core and the waist edge of the belt, the waist elastic bodies having elasticity over the entire transverse width of one or both the front belt and the back belt;

a plurality of lower elastic bodies disposed below the waist band elastic bodies and partially overlapping the absorbent core along side edges thereof, and removed of their elasticity in at least a portion overlapping the absorbent core; and at least one core edge elastic body disposed between the waist band elastic bodies and the lower elastic bodies, overlapping the absorbent core and having elasticity over the entire transverse width of the one or both the front belt and the back belt.

2. The article of claim 1 having two core edge elastic bodies disposed between the waist band elastic bodies and the lower elastic bodies, the two core edge elastic bodies being disposed in an interval in the longitudinal direction of no more than 4 mm, wherein each of the two core edge elastic bodies has a density of 540-1100 dtex, and is disposed at an elongation of from 150% to 300%.

3. The article of claim 2 wherein the core edge elastic bodies are disposed at a distance of from 1 mm to 30 mm away from the distal edge of the absorbent core.

4. The article of claim 1 wherein the waist band elastic bodies are disposed at a distance of from 2 mm to 20 mm of the distal edge of the absorbent core.

5. The article of claim 4 wherein each of the waist band elastic bodies has a density of 470-1100 dtex, and is disposed at an elongation of from 150% to 250%.

6. The article of claim 1 wherein the front belt comprises front waist band elastic bodies, front lower elastic bodies, and at least one front core edge elastic body.

7. The article of claim 6 wherein the at least one front core edge elastic body and a core edge elastic body of the back belt are disposed at different distances from the waist edge of the waist belt in the longitudinal direction.

8. The article of claim 1 wherein the lower elastic bodies have elasticity in regions overlapping the absorbent core adjacent the side edges thereof.

9. The article of claim 1 wherein at least some of the elastic bodies longitudinally outboard of the absorbent core are removed of its elasticity for at least a certain transverse width.

10. The article of claim 1 wherein a Waist Circumference Force according to the Whole Article Force Measurement herein is no more than 10 N.

11. The article of claim 1 wherein the length of the article along the longitudinal axis is no less than 350 mm.

12. The article of claim 1 wherein each of the leg edges and the waist edges of the front belt and the back belt are substantially parallel, the longitudinal length of the back belt being longer than that of the front belt, wherein the waist edge of the front belt is aligned with the waist edge of the back belt, and the leg edge of the front belt is not aligned with the leg edge of the back belt.

* * * * *